United States Patent
Min

[11] Patent Number: 5,785,648
[45] Date of Patent: Jul. 28, 1998

[54] SPECULUM

[75] Inventor: David Min, Munster, Ind.

[73] Assignee: David Min, M.D., Inc., Munster, Ind.

[21] Appl. No.: 728,084

[22] Filed: Oct. 9, 1996

[51] Int. Cl.⁶ .................................................... A61B 1/00
[52] U.S. Cl. ........................ 600/206; 600/223; 600/220; 600/219; 600/245
[58] Field of Search ..................... 600/206, 208, 600/220, 223, 219, 226, 235, 245, 201

[56] References Cited

U.S. PATENT DOCUMENTS

| | | |
|---|---|---|
| 471,990 | 3/1892 | Daily . |
| 559,122 | 4/1896 | Daily . |
| 605,652 | 6/1898 | Pitt . |
| 872,343 | 12/1907 | Griswold . |
| 872,344 | 12/1907 | Griswold . |
| 1,094,575 | 4/1914 | Joutras . |
| 1,222,478 | 4/1917 | Sheaff . |
| 1,706,500 | 3/1929 | Smith . |
| 2,247,258 | 6/1941 | Shepard . |
| 2,482,971 | 9/1949 | Golson . |
| 2,690,745 | 10/1954 | Govan . |
| 3,131,690 | 5/1964 | Innis et al. . |
| 3,324,850 | 6/1967 | Gunning et al. . |
| 3,532,088 | 10/1970 | Fiore . |
| 3,592,199 | 7/1971 | Ostensen . |
| 3,664,330 | 5/1972 | Deutsch . |
| 3,716,047 | 2/1973 | Moore et al. . |
| 3,744,481 | 7/1973 | McDonald . |
| 3,762,400 | 10/1973 | McDonald . |
| 3,789,835 | 2/1974 | Whitman . |
| 3,796,214 | 3/1974 | Davis . |
| 3,851,642 | 12/1974 | McDonald . |
| 4,067,323 | 1/1978 | Troutner et al. . |
| 4,086,919 | 5/1978 | Bullard . |
| 4,300,541 | 11/1981 | Burgin . |
| 4,337,763 | 7/1982 | Petrassevich . |
| 4,369,576 | 1/1983 | McVaugh . |
| 4,432,351 | 2/1984 | Hoary . |
| 4,434,800 | 3/1984 | Anson et al. . |
| 4,546,761 | 10/1985 | McCullough . |
| 4,567,881 | 2/1986 | Heller . |
| 4,597,383 | 7/1986 | VanDerBel . |
| 4,619,248 | 10/1986 | Walsh . |
| 4,638,792 | 1/1987 | Burgin . |
| 4,766,886 | 8/1988 | Juhn . |
| 4,896,661 | 1/1990 | Bogert et al. ............... 600/219 X |
| 5,054,906 | 10/1991 | Lyons, Jr. . |
| 5,143,054 | 9/1992 | Adair . |
| 5,165,387 | 11/1992 | Woodson . |
| 5,199,418 | 4/1993 | Jamison, Jr. et al. . |
| 5,251,613 | 10/1993 | Adair . |
| 5,297,538 | 3/1994 | Daniel ........................... 600/206 |
| 5,458,595 | 10/1995 | Tadir et al. . |
| 5,465,709 | 11/1995 | Dickie et al. . |
| 5,529,571 | 6/1996 | Daniel ......................... 600/245 X |

FOREIGN PATENT DOCUMENTS

| | | |
|---|---|---|
| 2302614 | 7/1974 | Germany . |
| 273809 | 6/1951 | Switzerland . |
| 25040 | 11/1913 | United Kingdom . |

*Primary Examiner*—Jeffrey A. Smith
*Attorney, Agent, or Firm*—Banner & Witcoff, Ltd.

[57] ABSTRACT

A speculum includes manually operated scissor arms with keyed shafts at the ends of each arm adapted to receive speculum jaw or blade members supported on the shaft in a desired, adjustable orientation. The speculum blades include a self-contained fiber optic light source. An optional sleeve with shape memory characteristics may be used in combination with the speculum jaw members.

13 Claims, 3 Drawing Sheets

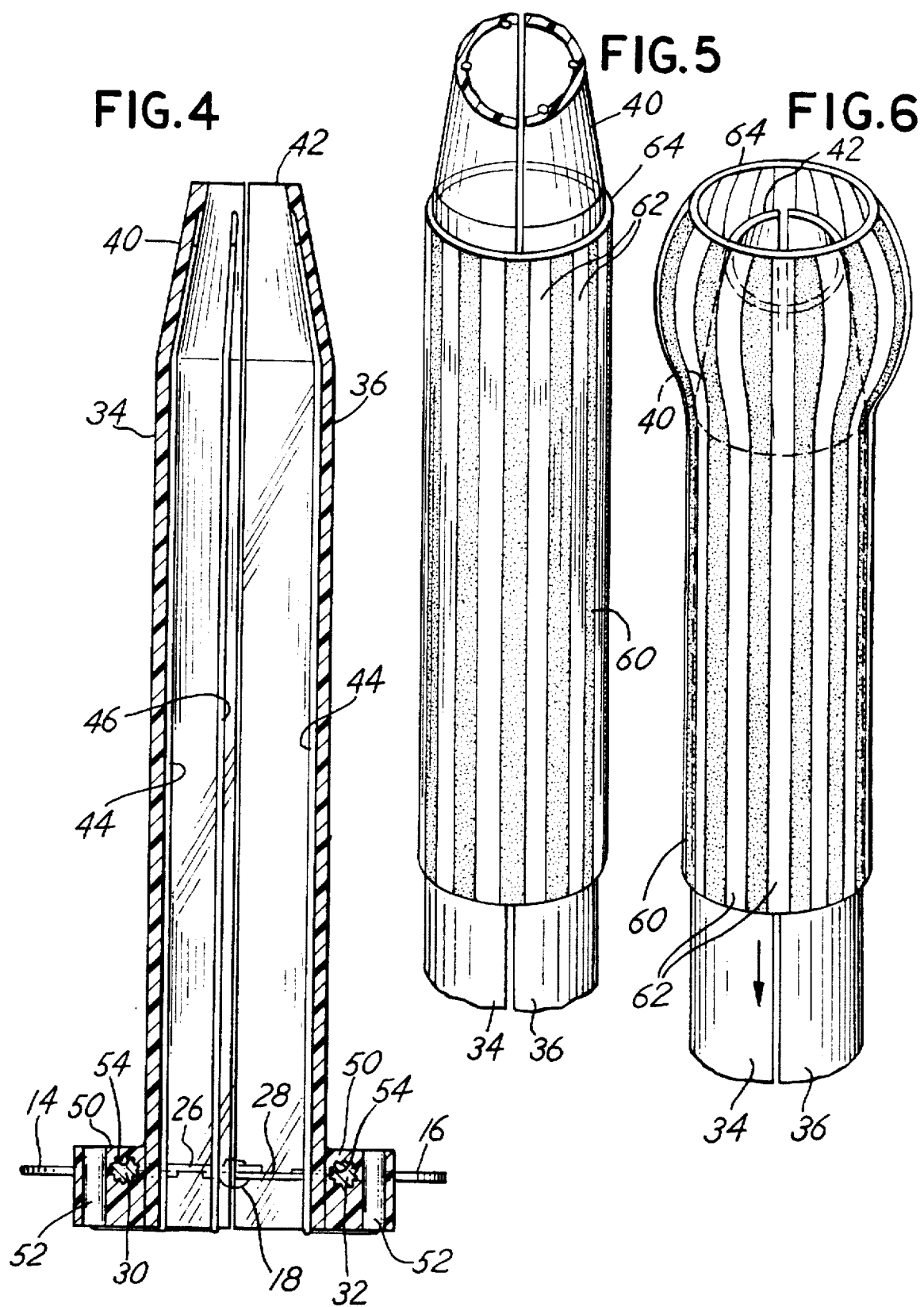

SPECULUM

BACKGROUND OF THE INVENTION

The principal aspect, the present invention comprises a medical instrument or speculum and, more particularly, a speculum of the type which may be used for vaginal examination; however, the principal of the invention may be utilized in instruments designed for other examination purposes such as oral examination, aural cavity examination and the like.

The utilization of medical instruments which facilitate the physical examination of a patient and generally described as a speculum or endoscopic instrument comprise a well known technique in medical examination procedures. An endoscope instrument used for such purposes is disclosed in U.S. Pat. No. 605,652 in the name of Pitt. There disclosed instrument is comprised of scissors-type handles which are manually operated to open and close speculum or endoscopic jaws having a semi-conical configuration. A light source is mounted within the jaws to facilitate the examination process when the jaws are inserted into a cavity and caused to spread by operation of the manual handles.

Various other instruments of this nature have been the subject of patent protection. Strauss, in U.S. Pat. No. 1,094,575, discloses a speculum of similar construction utilized for dental and oral examination purposes. Deutsch, in U.S. Pat. No. 3,664,330, discloses a speculum instrument which includes fiber optic elements carried in speculum jaw members which are designed to extend into a body orifice to provide illumination. McDonald, in U.S. Pat. No. 3,762,400, discloses a medical instrument of a similar configuration wherein the speculum members or jaws include removable legs adapted to receive fiber optic elements or bundles. The device disclosed in the McDonald patent is useful for vaginal inspection.

Over the years, there have been numerous additional patents granted for other instruments of this general nature, including the following:

| Pat. No. | Title | Inventor | Issue Date |
|---|---|---|---|
| 471,990 | Endoscopic Instrument | John W. Daily | March 29, 1892 |
| 559,122 | Endoscopic Instrument | John W. Daily | April 28, 1896 |
| 872,343 | Speculum | Frank E. Griswold | December 3, 1907 |
| 872,344 | Speculum | Frank E. Griswold | December 3, 1907 |
| 1,222,478 | Speculum | P. A. Sheaff | April 10, 1917 |
| 1,706,500 | Surgical Retractor | H. J. Smith | March 26, 1929 |
| 2,247,258 | Surgical Instrument | B. J. Shepard | June 24, 1941 |
| 2,482,971 | Self-Illuminated Transparent Proctoscope | K. K. Golson | September 27, 1949 |
| 2,690,745 | Tongue Blade | C. D. Govan | October 5, 1954 |
| 3,131,690 | Fiber Optics Devices | R. E. Innis et al. | May 5, 1964 |
| 3,324,850 | Illuminated Vaginal Speculum with Rotatable Cam Pivoting and Locking Means | J. E. Gunning et al. | June 13, 1967 |
| 3,532,088 | Speculum Instrument | John M. Fiore | October 6, 1970 |
| 3,592,199 | Autoclavable Surgical Instrument Illumination | Ralph G. Ostensen | July 13, 1971 |
| 3,716,047 | Disposable Light-Conductive Speculum | W. C. Moore et al. | February 13, 1973 |
| 3,744,481 | Medical Examining Method and Means | Bernard McDonald | July 10, 1973 |
| 3,789,835 | Illuminating Attachments For Vaginal Speculum | Robert S. Whitman | February 5, 1974 |
| 3,796,214 | Perineal Retractor | Rachel D. Davis | March 12, 1974 |
| 3,851,642 | Medical Examining Instrument | Bernard McDonald | December 3, 1974 |
| 4,086,919 | Laryngoscope | James R. Bullard | May 2, 1978 |
| DE 2,302,614 | | Metall et al. | January 19, 1973 |
| Swiss 273809 | Medical Instrument For Examining Human Body Cavities | Emile Vaurillon | June 19, 1951 |
| UK 25,040 | Light Speculum For Gynecological Purposes | R. Hammerschlag | November 3, 1913 |

While many instruments have been developed in this particular field, there has remained the need for a speculum instrument which is highly adjustable, capable of utilizing fiber optic lighting elements, and which includes disposable blades or speculum members that are inexpensive yet highly utilitarian.

SUMMARY OF THE INVENTION

Briefly, the present invention comprises a speculum which includes a first scissors arm pivotally connected to a second scissors arm. Each arm is substantially the mirror image of the other and includes a handle or manual gripping end, a support shaft end and a pivot intermediate the ends. Preferably a support shaft extends substantially transversely from the support shaft end of each scissors member and has a keyed cross sectional shape; for example, the support shaft is a splined shaft. Speculum jaw members or blades include throughbores at one end compatible with the posts or shafts extending from the scissors arms. Thus the bore of each of the speculum jaw members or blades is likewise configured or keyed so as to be adjustably positioned or orientable on the shaft. In this manner, the angular relationship of the jaw members or blades may be adjusted slightly depending upon medical needs or physician preference. A fiber optic package or bundle is included within each of the blades or jaw members. The jaw members are fabricated from sterile sanitary materials such as molded plastic materials and are disposable. As an additional feature of the invention, the speculum blades or jaw members may include a shape memory cylinder or element which fits over the blades, whereby upon insertion of the blades and cylinder into a body cavity, an adjustment of the cylinder may be made so as to cause the forward end of the cylinder to expand in a controlled fashion, thereby expanding the body cavity under examination in a desired manner to facilitate the examination procedure.

Thus it is the object of the invention to provide an approved medical instrument or speculum.

Yet a further object of the invention is to provide an improved speculum apparatus which permits manual operation of scissors members to spread speculum jaws that are replaceable and adjustable.

Yet a further object of the invention is to provide a speculum member having speculum blades which are removable and replaceable and which when removed or replaced are adjustable so as to adjust the angle or orientation of the blades relative to one another.

Yet a further object of the invention is to provide speculum instrument wherein the speculum blades include a self-contained energy source and fiber optic light elements to facilitate the use of the instrument when inspecting a cavity.

Another object of the invention is to provide an improved speculum instrument which includes speculum blades or speculum jaw members useful with a shape memory element which enhances the opportunity to utilize the speculum for diagnostic purposes.

These and other objects, advantages and features of the invention will be set forth in a detailed description as follows.

BRIEF DESCRIPTION OF THE DRAWING

In the detailed description that follows, reference will be made to the drawing comprised of the following figures:

FIG. 4 is a cross sectional view of the splined shaft utilized for mounting speculum blade members taken along the line 4—4 in FIG. 2, FIG. 5 is an isometric view of a sleeve which may be used co-jointly with the speculum instrument of the invention, said sleeve including a shape memory feature; and FIG. 6 is an isometric view of the sleeve of FIG. 5 wherein the speculum blade members are partially withdrawn from the sleeve so as to permit the shape memory feature to be activated, thereby enhancing cavity size by means of the instrument and sleeve.

DESCRIPTION OF THE PREFERRED EMBODIMENT

Figure 1:
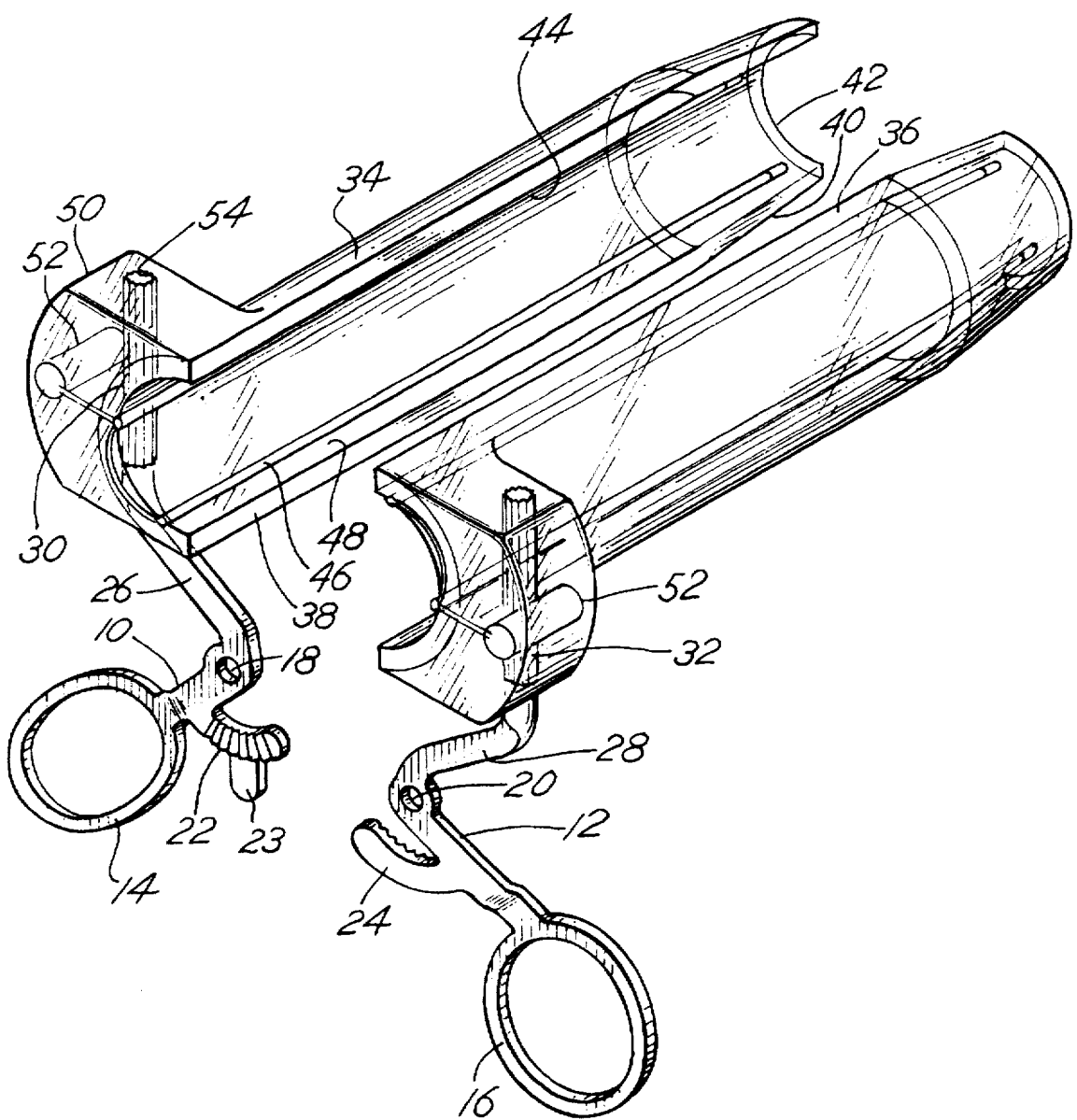
FIG. 1 is an exploded isometric view of an embodiment of the speculum instrument of the invention.
Figure 2:
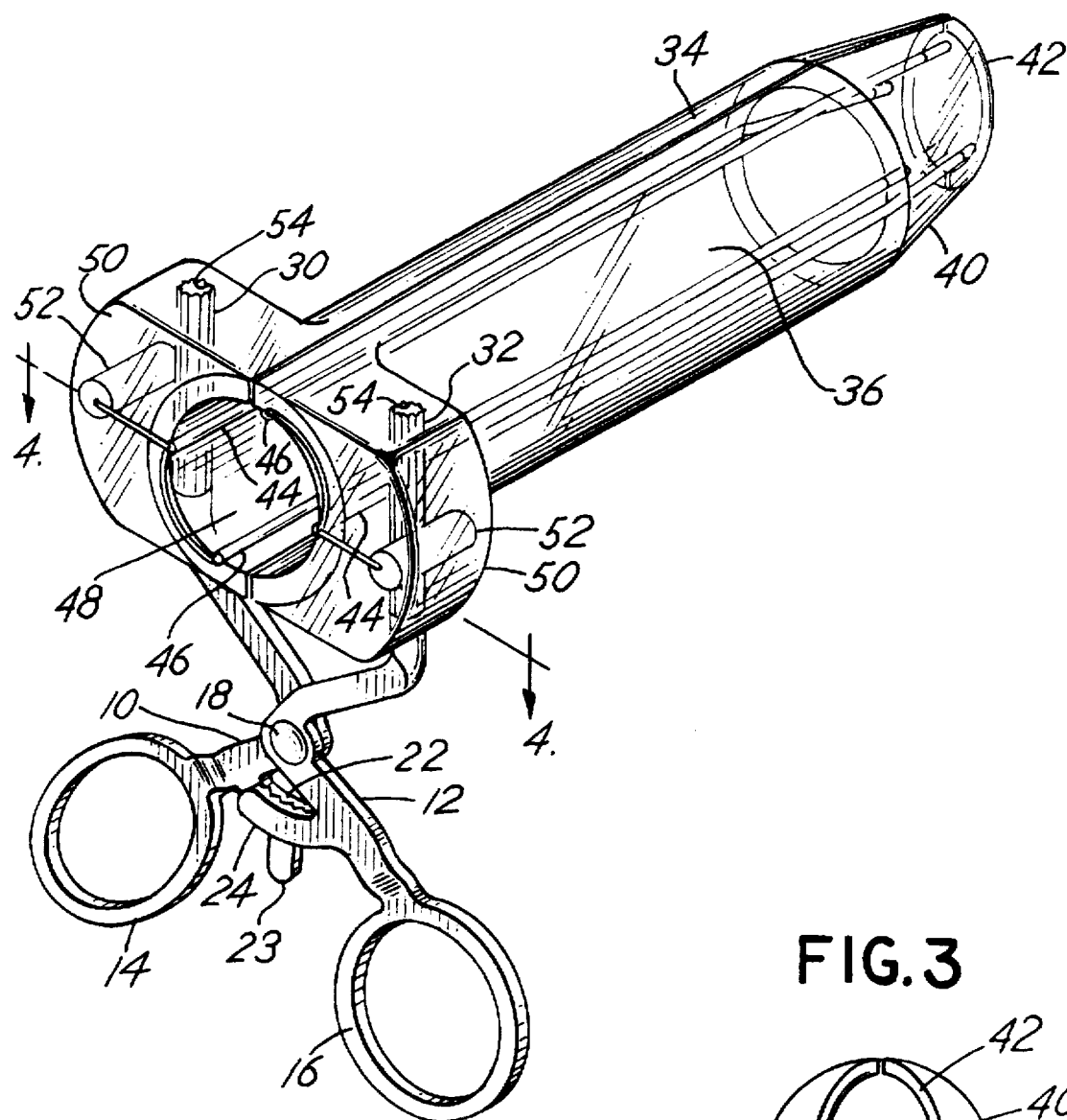
FIG. 2 is an isometric view of the instrument of FIG. 1 assembled for utilization.
Figure 3:
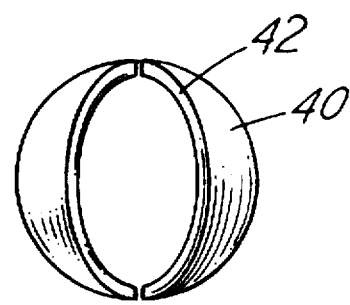
FIG. 3 is a front end view of the speculum blades or speculum jaw members utilized in the instrument of the invention.

The medical instrument or speculum of the present invention includes a first scissors arm 10 and a second compatible scissors arm 12 which is substantially a mirror image of arm 10. The scissors arm 10 includes a manually operable end or handle 14 which is shaped as to receive the fingers of a medical practitioner. Similarly, scissors arm 12 includes a manually operable handle or end 16. Scissors arm 10 further includes a pivot connection 18 as does arm 12 include a pivot connection 20. The pivot connections 18, 20 overlap and join together so that actuation of the handles 14, 16 will effect an appropriate scissors or spreading action. In the preferred embodiment, the arm 10 includes a projecting locking member 22 which cooperates with locking member 24 projecting from the scissors arm 12. The members 22 and 24 overlap one another and include serrated or locking ribs such that when the handles 14 and 16 are manually moved one toward the other, handles 14, 16 remain in a fixed or locked position so that the speculum jaw members will remain fixed in an open or locked position. A manually operated locking release tab 23 is provided to release one of the locking members 22 from the other locking member 24 when desired. Each scissors arm 10 and 12 further includes a projecting forward shaft or bracket support section or arm such as arm 26 of scissors arm 10 and arm 28 of scissors arm 12. The elements so far described are generally coplanar.

The support ends 26 and 28 of the respective scissors arms 10 and 12 include an upwardly projecting splined shaft 30 and 32 respectively. Each splined shaft 30 and 32 typically has a uniform cross section shape depicted in FIG. 4 by way of example. The particular configuration of the splined shaft 30, 32 depicted in FIG. 4 is not a limiting feature of the invention. Each shaft 30, 32 is shaped or keyed so as to maintain speculum members 34, 36 (described below) locked onto or attached to or supported by each shaft or post 30 and 32 respectively so as to be removable and replaceable and fixed or oriented in a fixed position when mounted on post 30, 32. The shafts 30, 32 may extend transversely from the ends 26, 28. Thus, the shafts 30, 32 extend at an angle from the plane of the arms 10, 12.

Thus mounted upon each post or shaft 30 and 32 is a separate speculum jaw member 34 and 36. In the practice of the invention, the speculum members 34 and 36 are substantially identical or mirror images of one another. In fact, in one embodiment, the members 34 and 36 are identical and may be reversed in orientation so as to be mounted on either post 30 or post 32. However, it is not necessary that the speculum members be identical. Thus a right-handed and a left-handed speculum member may be manufactured so as to provide for specialized operation of the instrument. The right-handed speculum member, for example, may be fore-shortened relative to the one on the left side. Thus the shapes and size of the separate speculum members may be varied depending upon medical needs. The number and intensity of the fiber optic packages described below in each of the speculum members may be varied or adjusted. The speculum members may include auxiliary passageways for insertion of medicaments, for example. Nonetheless, a description of speculum member, such as the left side speculum member 34, is generally applicable to the right side member 36.

Referring to the left side speculum member 34, the member 34 is generally comprised of a semi-cylindrical pre-molded or preformed material. Typically a plastic material may be used although it is possible to use other materials. The speculum member 34 includes a semi-cylindrical body 38 and a forward frusto-conical end 40 which terminates in a semi-elliptical or semi-cylindrical forward end 42. Fiber optic bundles or fibers 44 and 46 extend as light elements either on an internal surface 48 of the speculum member 34 or are retained within passages within the member 34. The material used to manufacture the speculum member 34 may be transparent or translucent so as to enhance the utility of the fiber optic light elements 44, 46.

A bracket member or bracket housing 50 is provided at the mounting end of the speculum blade or jaw member 34. The bracket 50 is connected to and supports the body 38. The bracket 50 also preferably includes a power source, such as a battery 52, which is connected to and provides power to the fiber optic light elements 44 and 46. Importantly, the bracket 50 includes a bore 54. The bore 54 has a cross-sectional shape, substantially identical to the cross-sectional shape of the post or shaft 32 such as depicted in FIG. 4 so that the speculum member 34 may be mounted on shaft 30 by sliding the opening or bore 54 over the post or shaft 30 and extend in a perpendicular direction from the shaft 30. Note that because of the configuration of the cross section of the post 30 and bore 54, it is possible to adjust the angle of attachment of the speculum member 34 relative to the angle of the attachment of the speculum member 36. Thus the members 34 and 36 may be aligned so as to be angled toward one another at their forward ends. Alternatively, they may be aligned in a parallel fashion or they may be splayed or extended outwardly relative to one another. Additionally, since the bore 54 may be a throughbore, the speculum member 34 may be inserted on either post 30 or 32. That is, the members 34 and 36 are reversible when a throughbore 54 of uniform cross section shape and size is provided and posts 30, 32 are identical.

However, it is possible to design the posts or shafts 30 and 32 so as to be distinct or different thereby keying left side and right side speculum members independently to posts 30 and 32. Further, it is possible to construct bore 54 so as to have a distinct configuration at each end and thus be compatible with distinct posts 30 and 32 should that be a desired feature.

In other words, by way of example, but not limitation, if the bore 54 includes a section or length at one end which has a cross section identical to the cross section of the shaft 30 and the shaft 30 is foreshortened or only one-half the length of the bore 54, then the member 34 can be fitted appropriately on the shaft 30 in a left side configuration as shown in FIG. 1. Then if the upper half of the bore 54 is configured so as to be compatible only with the configuration of a post 32 extending halfway therethrough and associated with the right hand side, the positioning of the speculum member 34 or the right hand side can be assured. Various other combinations and permutations of bore 54 configuration and shaft 30, 32 configuration may be utilized to accommodate desired orientations and assembly of speculum members 34, 36 to the respective shafts 30 and 32.

FIGS. 5 and 6 illustrate a further feature of the invention. There a cylindrical or elliptical or other closed sleeve member 60 is fitted over the speculum members 34 and 36 for insertion into the appropriate body cavity. The speculum members 34 and 36 may then be partially, longitudinally withdrawn from the sleeve 60. The sleeve 60 includes parallel segments 62 which are arranged circumferentially about the forward end 64 of the sleeve 60. The segments 62 have a shape memory characteristic and will, upon removal of blades 34, 36, balloon outwardly thereby smoothing out the contours of the cavity to provide for enhanced inspection and access. Again, the material utilized for the sleeve 60 may be transparent or translucent to enhance inspection.

While there has been set forth a preferred embodiment of the invention, it is understood that various changes may be made to the component or structural parts and their relationship including changes of the type described herein. Thus the invention is to be limited only by the following claims and their equivalents.

What is claimed is:

1. A speculum comprising, in combination:

a first scissors arm, including a manual gripping end and a support shaft end with a pivot connection intermediate the ends;

a second scissors arm, said second scissors arm including a manual gripping end aligned with the manual gripping end of the first arm, a support shaft end and a pivot connection intermediate the ends, said scissors arms pivotally attached at the pivot connection whereby as the gripping ends move together, the support shaft ends move apart and vice versa;

a first keyed support shaft extending from the support shaft end of the first arm;

a second keyed support shaft extending from the support shaft end of the second arm, said first and second shafts being generally parallel;

a first speculum member having a mounting end and an insertion end, said mounting end including a mounting bracket with a keyed bore for receipt of the first support shaft; and a second speculum member having a mounting end and an insertion end, said mounting end including a mounting bracket with a keyed bore for receipt of the second support shaft whereby the speculum members are in opposed relation and spread when the gripping ends of the scissors arms approach each other, at least one of said keyed bores being shaped to receive one of said support shafts in more than one orientation.

2. The speculum of claim 1 wherein the scissors arms pivot in a plane and the support shafts extend generally at an angle from the plane of the scissors arms.

3. The speculum of claim 2 wherein the support shafts extend generally transversely from the plane.

4. The speculum of claim 1 wherein the speculum members are substantially identical and are affixed to the first and second support shafts respectively in opposed, mirror image relation.

5. The speculum of claim 1 wherein at least one speculum member is comprised of a longitudinal, arcuate section of a tube.

6. The speculum of claim 1 wherein the keyed bore of at least one speculum member is adjustably keyed to one of said support shafts.

7. The speculum of claim 1 further including a power source in one of said speculum members and a light source powered by the power source and positioned for lighting a cavity into which the speculum is fitted.

8. The speculum of claim 1 further including scissors clamp members interacting between the scissors arms for maintaining the scissors arms and speculum members in a manually adjusted, fixed position.

9. The speculum of claim 1 wherein the support shafts are parallel and aligned to extend in a perpendicular direction from their respective support shaft ends of the scissors arms, and said speculum members are each adjustably keyed to a support shaft and extend in a perpendicular direction therefrom.

10. The speculum of claim 1 wherein the bore in each mounting bracket is a throughbore with a keyed passage and each speculum member is substantially identical and reversibly mounted on one support shaft or the other.

11. The speculum of claim 1 wherein the bore in each mounting bracket is a throughbore which has a unique key shape at each end of the bore compatible with one or the other support shaft.

12. The speculum of claim 1 wherein at least one speculum member includes a fiber optic member for transmitting a wave energy source from the speculum member.

13. The speculum of claim 1 further including a sleeve longitudinally insertable over the speculum members, said sleeve including a shape memory section which is activated upon removal of the blade members from said section.

\* \* \* \* \*